(12) United States Patent
Agustsson et al.

(10) Patent No.: US 12,137,514 B2
(45) Date of Patent: Nov. 5, 2024

(54) LINEAR ACCELERATOR FOR GENERATING HIGH X-RAY DOSES

(71) Applicant: RadiaBeam Technologies, LLC, Santa Monica, CA (US)

(72) Inventors: Ronald Agustsson, Venice, CA (US); Salime Boucher, Santa Monica, CA (US); Sergey Kutsaev, Santa Monica, CA (US)

(73) Assignee: RadiaBeam Technologies, LLC, Santa Monica, CA (US)

( * ) Notice: Subject to any disclaimer, the term of this patent is extended or adjusted under 35 U.S.C. 154(b) by 0 days.

(21) Appl. No.: 17/754,764

(22) PCT Filed: Dec. 2, 2020

(86) PCT No.: PCT/US2020/062835
§ 371 (c)(1),
(2) Date: Apr. 11, 2022

(87) PCT Pub. No.: WO2021/113323
PCT Pub. Date: Jun. 10, 2021

(65) Prior Publication Data
US 2024/0090112 A1      Mar. 14, 2024

Related U.S. Application Data

(60) Provisional application No. 62/944,574, filed on Dec. 6, 2019.

(51) Int. Cl.
*H05H 7/04* (2006.01)
*H05H 9/04* (2006.01)

(52) U.S. Cl.
CPC ............ *H05H 7/04* (2013.01); *H05H 9/048* (2013.01); *H05H 2007/048* (2013.01); *H05H 2277/11* (2013.01)

(58) Field of Classification Search
None
See application file for complete search history.

(56) References Cited

U.S. PATENT DOCUMENTS

| | | | | |
|---|---|---|---|---|
| 11,612,049 | B2 * | 3/2023 | Agustsson | H05H 9/048 |
| 11,737,202 | B2 * | 8/2023 | Liu | H05H 7/02 |
| | | | | 315/505 |
| 11,800,631 | B2 * | 10/2023 | Agustsson | H05H 9/00 |
| 2007/0086569 | A1 | 4/2007 | Johnsen | |

(Continued)

OTHER PUBLICATIONS

International Search Report and Written Opinion of PCT/2020/062835, dated Feb. 25, 2021 in 8 pages.
M. Aicheler, et al., "A Multi-TeV Linear Collider Based on CLIC Technology: CLIC Conceptual Design Report," CERN-2012-007 (2012).
J. Bourhis, et al., "Clinical translation of FLASH radiotherapy: Why and how?," Radiother. Oncol. vol. 139: p. 11-17 (2019).

(Continued)

*Primary Examiner* — Srinivas Sathiraju
(74) *Attorney, Agent, or Firm* — Knobbe, Martens, Olson & Bear, LLP

(57) ABSTRACT

An X-ray generation system is configured to generate an X-ray beam configured to be delivered to a patient undergoing radiation therapy. The X-ray generation system includes a linear accelerator system configured to generate an electron beam configured to impinge a target configured to respond to the incident electron beam by emitting an X-ray beam configured to deliver an X-ray dose rate to the patient in a range of 40 Gy/s to 1000 Gy/s within a treatment delivery window.

24 Claims, 10 Drawing Sheets

(56) References Cited

U.S. PATENT DOCUMENTS

| | | | | |
|---|---|---|---|---|
| 2008/0129203 | A1* | 6/2008 | Agustsson | H01J 23/005 315/5 |
| 2008/0179519 | A1* | 7/2008 | Andonian | G02F 1/132 250/331 |
| 2011/0240888 | A1* | 10/2011 | Rosenzweig | G01R 31/2881 250/492.1 |
| 2011/0290379 | A1* | 12/2011 | Murokh | H01F 1/053 148/559 |
| 2012/0294423 | A1* | 11/2012 | Cheung | H05H 9/02 378/65 |
| 2014/0119496 | A1* | 5/2014 | Zhou | A61N 5/1069 378/65 |
| 2015/0338545 | A1* | 11/2015 | Arodzero | G01N 23/04 378/57 |
| 2017/0093113 | A1* | 3/2017 | Musumeci | H01S 3/0959 |
| 2017/0336526 | A1* | 11/2017 | Arodzero | G01V 5/232 |
| 2018/0279461 | A1* | 9/2018 | Agustsson | A61N 5/1045 |
| 2019/0129060 | A1* | 5/2019 | Arodzero | G01V 5/224 |
| 2019/0320523 | A1* | 10/2019 | Agustsson | G21K 1/046 |
| 2020/0068699 | A1* | 2/2020 | Kutsaev | H05H 7/12 |
| 2020/0092979 | A1* | 3/2020 | Agustsson | H05H 9/02 |
| 2020/0094078 | A1* | 3/2020 | Sheng | A61N 5/1031 |
| 2020/0221567 | A1* | 7/2020 | Agustsson | G21K 1/046 |
| 2021/0204389 | A1* | 7/2021 | Agustsson | H05H 9/02 |
| 2021/0219413 | A1* | 7/2021 | Agustsson | G21K 1/046 |
| 2022/0023667 | A1* | 1/2022 | Sheng | A61N 5/1083 |
| 2022/0039246 | A1* | 2/2022 | Agustsson | H05H 9/044 |
| 2022/0223778 | A1* | 7/2022 | Kutsaev | H10N 60/12 |
| 2023/0082826 | A1* | 3/2023 | Agustsson | H05H 9/044 315/505 |

OTHER PUBLICATIONS

J. Bourhis et al., "Treatment of a first patient with FLASH-radiotherapy," Radiother. Oncol. http://doi.org/10.1016/j.radonc.2019.06.019 (2019).

S. Döbert, "High-efficiency L-band klystron development for the CLIC drive beam in CLIC workshop," CERN, Geneva Switzerland, 32 pages (2018).

V. Favaudon et al., "Ultrahigh dose-rate FLASH irradiation increases the differential response between normal and tumor tissue in mice," www.ScienceTranslationMedicine.org, vol. 6, Issue 245 (2014).

P. Montay-Gruel et al., "Irradiation in a flash: Unique sparing of memory in mice after whole brain irradiation with dose rates above 100 Gy/s," Radiother. Oncol. http://dx.doi.org/10.1016/j.radonc.2017.05.003 (2017)).

National Council on Radiation Protection and Measurements, "Radiation protection design guidelines for 0.1-100 MeV particle accelerator facilities: recommendations of the National Council on Radiation Protection and Measurements," NCRP report No. 51, Washington: The Council. vii, 159 p. (1977).

R. Shende et al., "Commissioning of TrueBeam™ Medical Linear Accelerator: Quantitative and Qualitative Dosimetric Analysis and Comparison of Flattening Filter (FF) and Flattening Filter Free (FFF) Beam," Int'l J. Med. Phys., Clinical Eng. and Rad. Oncol., 5, 51-69 (2015).

L. Skinner et al., "Tungsten filled 3D printed field shaping devices for electron beam radiation therapy," PLoS ONE 14(6):e0217757, https://doi.org/10.1371/journal.pone.0217757 (2019).

M-C. Vozenin et al., "The Advantage of FLASH Radiotherapy Confirmed in Mini-pig and Cat-cancer Patients," Am. Assoc. Cancer Res., doi: 10.1158/1078-0432 CCR-17-3375 (2018).

M.C. Vozenin, et al., "Biological Benefits of Ultra-high Dose Rate FLASH Radiotherapy: Sleeping Beauty Awoken," Clin. Oncol. (R. Coll. Radiol.), vol. 31(7), p. 407-415 (2019).

\* cited by examiner

LINEAR ACCELERATOR FOR GENERATING HIGH X-RAY DOSES

CLAIM OF PRIORITY

This application claims the benefit of priority to U.S. Provisional Appl. No. 62/944,574 filed on Dec. 6, 2019 and which is incorporated in its entirety by reference herein.

BACKGROUND

Field

This application relates to systems and methods for X-ray radiation therapy.

Description of the Related Art

Cancer is a global problem, accounting for almost 13% of all deaths worldwide and is one of the fastest growing diseases on earth. Radiation therapy (RT) by external beams, as primary treatment or in conjunction with chemotherapy, surgery or other modalities, is used to treat over 60% of cancer patients and used in nearly half of the curative cases.

The goal of RT is to deliver fatal doses of radiation to cancer cells while sparing healthy cells. The degree to which the dose distribution is confined to the cancer is called conformality. Serious, even fatal, side effects can result if healthy tissues are irradiated. RT uses intricately shaped dose distributions designed by a computer and delivered by a linear accelerator ("linac") from many angles around the patient, with adjustable apertures (e.g., multi-leaf collimator assemblies) that can precisely control the spatial distribution of the radiation. The dose distribution accuracy can be enabled by the use of precise imaging, for example, magnetic resonance imaging (MRI), computed tomography (CT), and positron emission tomography (PET), both before and during treatment.

SUMMARY

In one aspect, certain implementations described herein provide an X-ray generation system configured to generate an X-ray beam configured to be delivered to a patient undergoing radiation therapy. The X-ray generation system comprises an linear accelerator system configured to generate an electron beam configured to impinge a target configured to respond to the incident electron beam by emitting an X-ray beam configured to deliver an X-ray dose rate to the patient in a range of 40 Gy/s to 1000 Gy/s within a treatment delivery window.

In another aspect, certain implementations described herein provide an X-ray generation system configured to generate an X-ray beam configured to be delivered to a patient undergoing radiation therapy. The X-ray generation system comprises a controllably rotatable gantry having a rotation axis about which a rotatable portion of the gantry is configured to rotate. The rotation axis is configured to extend through the patient undergoing radiation therapy. The X-ray generation system further comprises a single linac configured to generate an electron beam. The X-ray generation system further comprises a target mounted in or on the rotatable portion of the gantry and configured to generate an X-ray beam in response to being irradiated by the electron beam. The X-ray beam is configured to irradiate the patient with an X-ray dose rate in a range of 40 Gy/s to 1000 Gy/s within a treatment delivery window. The X-ray generation system further comprises an electron optics sub-system comprising at least one magnet mounted in or on the rotatable portion of the gantry. The electron optics sub-system is configured to direct the electron beam from propagating in a first direction from the linac to propagating in a second direction towards the target.

In another aspect, certain implementations described herein provide an X-ray generation system configured to generate an X-ray beam configured to be delivered to a patient undergoing radiation therapy. The X-ray generation system comprises a gantry configured to extend at least partially around the patient undergoing radiation therapy. The X-ray generation system further comprises a single linac configured to generate an electron beam. The X-ray generation system further comprises a plurality of targets mounted in or on the gantry. Each target of the plurality of targets is configured to generate an X-ray beam in response to being irradiated by the electron beam. The X-ray beams from the plurality of targets are configured to irradiate the patient. The X-ray generation system further comprises an electron optics sub-system mounted in or on the gantry. The electron optics sub-system comprises at least one controllably switchable magnet configured to receive the electron beam propagating in a first direction from the linac and to deflect the electron beam into a selected one of two or more second directions. The electron optics sub-system further comprises two or more pluralities of magnets. Each plurality of magnets of the two or more pluralities of magnets is configured to receive the electron beam propagating in one of the two or more second directions from the at least one controllably switchable magnet and to direct the electron beam to propagate in a corresponding third direction towards a target of the plurality of targets.

DETAILED DESCRIPTION

Overview

Figure 1:
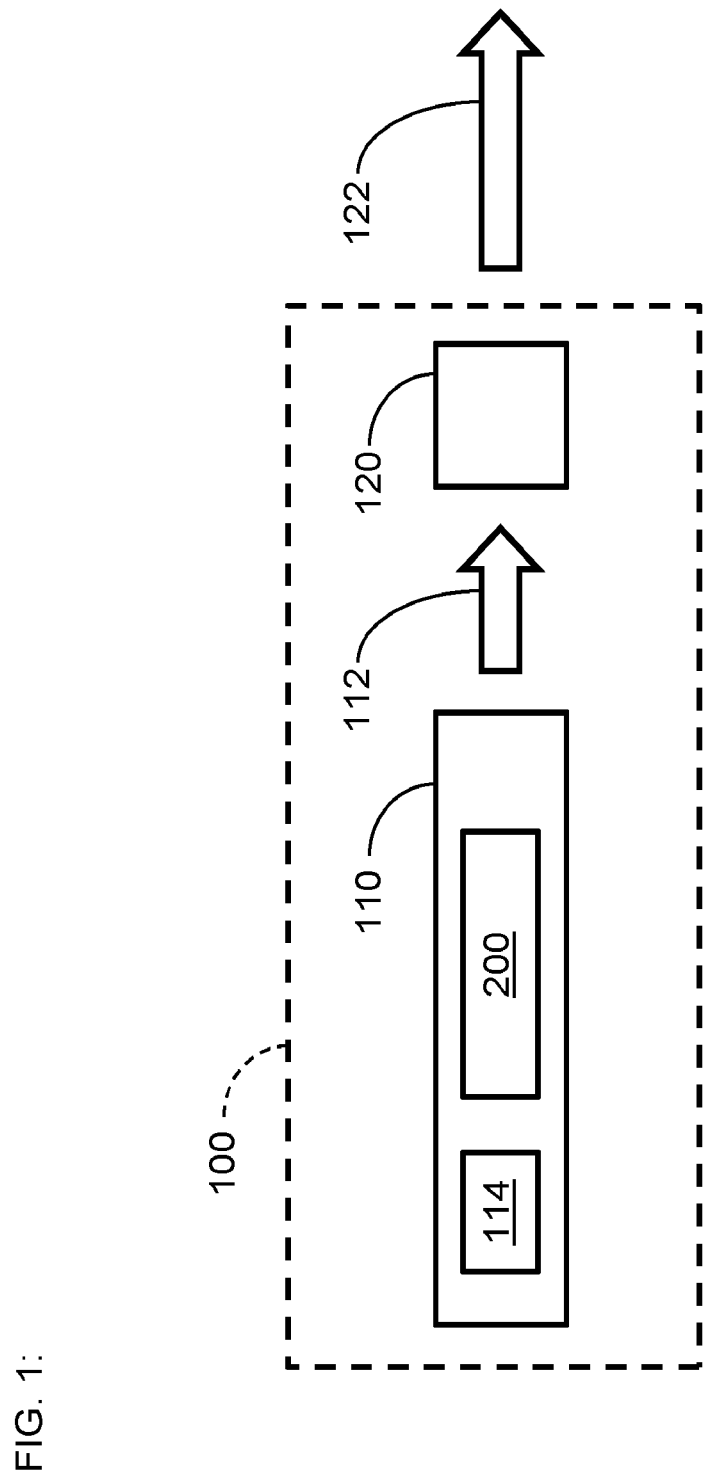
FIG. 1 schematically illustrates an example X-ray generation system in accordance with certain implementations described herein.

Novel approaches are constantly being developed to further improve conformality of RT. For example, particle beams (e.g., proton and carbon ion beams) of a certain energy will stop at a precise point, rather than being slowly attenuated like X-rays. Therefore, such particle beams can be used to achieve extremely low doses to healthy tissues while still reaching the desired dose to the tumor. However, proton and carbon ion therapy systems are much more expensive than standard linac systems, and suffer from range uncertainty, which partially counteracts the benefit of the precise stopping point provided by such particle beams.

Another, more recently discovered, factor in sparing healthy tissue is the time in which the radiation is delivered. RT works directly by ionizing atoms in DNA and other cellular targets, and works indirectly by creating reactive oxygen species (ROS) and other destructive free radicals that then go on to create damage in the cell. Radiation is most effective when it is delivered within a time period that is less than the cell's repair time; that way resulting damage (e.g., breaks in the DNA strand) are more likely to be fatal to the target tissue (e.g., cells). Beyond this time scale, it was not believed that there were other time-dependent effects.

Recently, however, it has been discovered that radiation delivered in very short time-scales (e.g., within time periods that are less than 1 second) is less damaging to healthy tissue, while being equivalently damaging to cancer cells. This technique has been referred to as "FLASH radiotherapy" or "FLASH RT".

The mechanisms of this effect are not completely understood, however, without being bound to any particular theory or mode of operation, the hypotheses include:
    Oxygen depletion leading to radioresistivity;
    Reduced radiation exposure of circulatory cells, which are important to the normal tissue repair and anti-cancer immunity;
    Dependence of inflammatory/anti-inflammatory cell signaling on treatment time; and
    Different tumor and normal cells radiation damage and repair mechanisms.

Regardless of the mechanism, the initial results have been extremely promising. Significantly lower toxicity has been shown in mice (see, e.g., V. Favaudon et al., "Ultrahigh dose-rate FLASH irradiation increases the differential response between normal and tumor tissue in mice," www.ScienceTranslationMedicine.org, Vol. 6, Issue 245 (2014); P. Montay-Gruel et al., "Irradiation in a flash: Unique sparing of memory in mice after whole brain irradiation with dose rates above 100 Gy/s," Radiother. Oncol. http://dx.doi.org/10.1016/j.radonc.2017.05.003 (2017)), pigs and cats (see, e.g., M-C. Vozenin et al., "The Advantage of FLASH Radiotherapy Confirmed in Mini-pig and Cat-cancer Patients," Am. Assoc. Cancer Res., doi: 10.1158/1078-04 32.CCR-17-3375 (2018)), and recently, the first human patient was reported (see, e.g., J. Bourhis et al., "Treatment of a first patient with FLASH-radiotherapy," Radiother. Oncol. http://doi.org/10.1016/j.radonc.2019.06.019 (2019)).

The dose selected for treating tumors is usually in the range of 10 Gy to 100 Gy, and the dose rate to deliver such doses in less than one second is on the order of 100 Gy/s. Such dose rates are achievable with electrons from a linear accelerator, however, electrons do not penetrate very far into tissue. Therefore, the research with electrons has only been done with small animals (e.g., mice) or on skin effects.

Some groups are attempting to use proton accelerators to deliver FLASH RT, however, apart from the downside in terms of cost and availability, proton accelerators cannot deliver the entire selected treatment dose within one second. Rather, the treatment must be broken up into many separate spots and/or fields that are delivered in sequence, and the total treatment times are expected to be on the order of minutes.

In certain implementations described herein, X-rays are generated for use in FLASH RT. X-rays can be an optimal tool for FLASH radiotherapy: more than 90% of all RT is delivered with X-rays, and X-rays are the most versatile and cost-effective form of radiation therapy. Unfortunately, the physical process for generating X-rays is not very efficient, so high power accelerators are used. Furthermore, it is desirable to treat using X-rays with as much conformality as possible. Conformality, in combination with the healthy-tissue-sparing FLASH effect, promise to dramatically improve patient outcomes.

Example Implementations of a Linac System for FLASH RT

Certain implementations described herein provide a linac configured to deliver X-ray doses that are on the order of 100 Gy in one second. Conventional medical linacs (e.g., electron beam energies of 6 MeV) are on the low end of the spectrum of linac powers, e.g., producing a flattening filter free dose rate of about 0.2 Gy/s at a position one meter from the X-ray target, which is about a factor of 500 too low for FLASH RT. By way of comparison, a conventional medical linac has a beam power on the order of 1 kW, while industrial linear accelerators (e.g., for sterilization of food and medical products) can achieve beam powers of several hundred kW.

In certain implementations, the electron beam energy is increased to improve the dose rate (e.g., energies of at least 10 MeV; energies of at least 20 MeV). The conversion efficiency of electron beam power to X-ray power scales approximately with the third power of the electron beam energy ($E_{electron}^3$) Therefore, a small increase in the electron beam energy can provide a large increase in the X-ray intensity. In addition, by increasing the electron beam energy, the resultant X-ray beam has an increased X-ray energy, which penetrates deeper into tissue. However, such increased X-ray energies can produce two negative (e.g., detrimental) effects: (i) a larger lateral penumbra of the X-ray beam, which is a measure of the fuzziness at the edge of the X-ray beam, and which degrades the conformity of the treatment, and (ii) greater neutron production, which can cause activation and unwanted dose to the patient and the environment. In certain implementations described herein, the electron beam energy, and the corresponding resultant X-ray beam energy, is selected to be 10 MeV to provide a sufficiently high dose rate while sufficiently reducing (e.g., minimizing) the negative factors.

In certain implementations, the distance from the source to the patient (e.g., which can be referred to as the source to skin distance or SSD) can be reduced to provide higher X-ray intensities at the target tissue, but practically, this distance has a lower limit. For example, to achieve good conformality, one or more collimator assemblies can be placed between the beam source and the patient, and to produce a small penumbra, the source to collimator distance (SCD) is selected to be as large as possible. These physical constraints, along with pure physical limitations on fitting the equipment around the patient, tend to limit the SSD to be 80 cm or greater. For purposes of comparing certain implementations described herein, the dose rates at an SSD of 100 cm can be compared to one another. In the description herein of the various implementations, the SSD is assumed to be at 100 cm unless otherwise specified.

FIG. 1 schematically illustrates an example X-ray generation system 100 in accordance with certain implementations described herein. The system 100 comprises an linear accelerator ("linac") system 110 configured to generate an electron beam 112 (e.g., having an electron beam energy in a range of 6 MeV to 25 MeV (e.g., substantially equal to 10 MeV) configured to impinge a target 120 configured to respond to the incident electron beam 112 by emitting an X-ray beam 122 (e.g., to be delivered to a patient undergoing RT) with an X-ray dose rate in a range of 40 Gy/s to 1000 Gy/s (e.g., substantially equal to 400 Gy/s) within a treatment delivery window.

In certain implementations, the linac system 110 comprises an S-band linac, while in certain other implementations, the linac system 110 comprises an L-band linac (e.g., which can be larger, and can achieve higher duty cycles and current/dose outputs, than do S-band linacs). Table 1 lists some other example parameters of the example linac system 110 in accordance with certain implementations described herein. These values are applicable during the very brief (e.g., less than or equal to 1 second; substantially equal to 1 second; in a range of 0.5 s to 1.5 s) window for treatment delivery, during which a burst of multiple pulses is emitted from the linac system 110. The dose rate factor in Table 1 has a relatively large range because the conversion factor scales approximately with energy cubed.

TABLE 1

| Example Parameters | Example Values | Example Ranges |
|---|---|---|
| Electron Beam Energy [MeV] | 10 | 6-25 |
| X-Ray Dose Rate [Gy/s] | 400 | 40-1000 |
| Dose Rate Factor [cGy/min/mA] | 4.50E+04 | 1.5E+04-3.00E+05 |
| Electron Beam Average Current [A] | 0.05 | 0.01-0.2 |
| Duty Cycle | 0.025 | 0.001-0.04 |
| Pulse Length [µs] | 167 | 4-400 |
| Repetition rate [Hz] | 150 | 50-2500 |
| Dose per pulse [Gy] | 2.67 | 0.02-10.0 |
| Instantaneous dose rate in pulse [Gy/s] | 1.6E+04 | 5.0E+03-1.0E+06 |
| Peak electron beam current on target [A] | 2.1 | 0.2-10 |
| Transmission | 33% | 10%-99% |
| Injected current [A] | 6.5 | 0.5-50 |
| Peak Beam Power [MW] | 21.3 | 5-60 |

For example, the linac system 110 of certain implementations described herein utilizes a duty cycle of 0.01, which is higher than the duty cycles of conventional medical linacs (e.g., 0.001). In certain implementations, this duty cycle is only maintained for a relatively short treatment time period (e.g., one second or less), and the linac system 110 can be dormant (e.g., not emitting the electron beam 112) for many minutes between treatment time periods during which the linac system 110 is emitting the electron beam 112. The example injected current of 6.5 A of Table 1 is higher than injected currents routinely achieved in other systems (e.g., injected currents of 2 A).

In certain implementations, as schematically illustrated by FIG. 1, the linac system 110 comprises an electron source 114 and at least one electron accelerating structure 200. The electron source 114 is configured to generate electrons and to pre-accelerate the electrons with DC or RF fields to energies in the range from tens of keV (e.g., for DC fields) to few MeV (e.g., with RF fields). The at least one accelerating structure 200 is configured to receive the electrons from the electron source 114 and to accelerate, bunch, and/or focus the electrons to form the electron beam 112 having a predetermined electron beam energy. While not shown in FIG. 1, the linac system 110 of certain implementations can also comprise other features, including but not limited to: one or more pre-accelerator sections (e.g., a bunching structure, either ballistic or waveguide or both, configured to accelerate, bunch, and/or focus the electrons); one or more ballistic buncher sections comprising a single RF cavity configured to operate at the same frequency $f_0$ as the accelerating structure or at a harmonic or sub-harmonic frequency (e.g., $f_0/2$) and with voltages about one-half of the electron gun voltage (e.g., 10-100 kV); one or more waveguide buncher sections comprising iris-loaded waveguide cells or other accelerating structures and configured to operate at either constant or variable phase velocities (e.g., 30%-99% of the speed of light) and with an RF field amplitude profile different from that of the accelerating sections and optimized for bunch shaping (e.g., 10%-200% of the accelerating gradient); one or more chopper sections (e.g., RF deflector with a slit and operating at the same frequency $f_0$ as the accelerating structure or at a harmonic or sub-harmonic frequency) having geometric dimensions and field amplitudes (e.g., 10 kV-few MV) configured to shorten bunch phase length and to reduce (e.g., eliminate) beam tails which can contaminate the following accelerating structure, one or more solenoids (e.g., having a magnetic field of 1000 G or more) configured to focus the electrons during capture and acceleration; one or more phase compressor sections comprising disk-loaded waveguides or similar accelerating structures with the bunch located in the phase φ that corresponds to $E(\varphi)=0$ and which accelerates the particles behind this phase and decelerates the particles ahead of this phase; one or more travelling wave or standing wave linac sections comprising iris-loaded waveguides or other accelerating structures configured to move the bunch synchronously with the high field electromagnetic wave (e.g., 5-500 MV/m) in accelerating phase (e.g., $qE(\varphi)>0$) and to receive the energy from this wave. In addition, the at least one electron accelerating structure 200 is connected to one or more RF power sources (e.g., klystrons, magnetrons, CFA, IOT, solid-state sources, etc.) configured to provide the radiofrequency energy used by the at least one electron accelerating structure 200. For example, commercially available klystrons in accordance with certain implementations described herein include, but are not limited to: VKS-8245B klystrons for RF power of 20 MW and VKS-8265A klystrons for RF power greater than or equal to 40 MW, both available from CPI (Communications & Power Industries) of Palo Alto, CA. In L-band, commercially available klystrons include, but are not limited to: TH 2104U and TH1803 from Thales (Velizy-Villacoublay, France), the E3736 and E37503 from Toshiba (Otawara, Japan) and the VKL-8301 from CPI.

In certain implementations, the electron source 114 comprises an electron gun having an EIMAC Y-646 cathode and is configured to provide (e.g., inject) electrons to the at least one electron accelerating structure 200 with electron beam currents that are equal to or greater than 10 A. Alternatively, the electron source 114 can comprise a YU-156 cathode that is configured into an electron gun with anode shaping and anode-cathode spacing optimized using computer simulations (e.g., EGUN or CST). For example, a well optimized geometry for such a gun is termed a Pierce gun. The cathode is at a relative negative potential with respect to the anode (e.g., approximately 100 kV; in a range of 30 kV to 200 kV). The cathode can be configured with a grid that is configured to allow adjusting the current while keeping the cathode-anode potential constant.

Repelling space charge forces of the high current beam can cancel the accelerating/extracting field near the cathode.

Therefore, in certain implementations, the design of the electron gun and/or the design of the anode shape can be configured to provide a high perveance (e.g., maximum current extracted for a certain voltage $I/U^{3/2}$).

Space charge repelling forces reduce with the beam energy increase in main accelerating structure, but between the electron gun and the accelerating structure, the beam can be very vulnerable to such space charge forces. To reduce the destructive effects of such space charge forces, a low-energy beam transport line (LEBT) can be used. An example LEBT line compatible with certain implementations described herein can include some or all of the following elements:

focusing lenses (e.g., solenoid, quadrupoles) configured to prevent the beam from blow-up;

defocusing elements configured to avoid transport of a small beam (e.g., to reduce space charge forces which are inversely proportional to beam cross section);

ballistic RF buncher (e.g., RF TM-class cavity) with a drift section configured to transform a continuous beam into short bunches, separated by a wavelength of a bunching cell frequency (pre-bunched beams can be better accepted into acceleration regime in main accelerating section, and can thus provide better transmission and energy spectrum, and can reduce beam loading and destructive space charge effects);

de-buncher configured to stretch the bunch and to reduce space charge effects during the transport;

re-buncher configured to compress the bunch before entering the accelerating section;

chopper (e.g., RF TE-class cavity with a slit) configured to minimize bunch length and/or to purify the beam spectrum by removing particles that are outside a certain phase distance from the bunch core;

focusing solenoids configured to contain the beam on the axis of the accelerating structure, to reduce the wakefield effects of the deflecting modes in these structures and therefore avoid the beam-blow up (BBU) effect, when such wakefields (caused by the particles travelling off-axis) build-up during the RF pulse and become strong enough to deflect the beam away from the aperture;

waveguide buncher comprising a tapered (e.g., variable phase velocity or/and field strength along the structure) RF accelerating structure (such as disk-loaded structure or any derivatives, including: biperiodic structures, side-coupled structure, disk-and-washer-structures, backward travelling wave structure, magnetic coupled structures, etc.) operating in either standing or travelling wave (e.g., forward or backward, fundamental or higher spatial or frequency harmonics). This buncher can be configured to bunch and accelerate the beam simultaneously, therefore increasing the accelerator efficiency both in terms of accelerating gradient (e.g., length) and space charge effects. This buncher can be used either separately or in combination with the ballistic buncher, or can be integrated into the main accelerating structure. A tapered phase velocity buncher can be used for high current linacs to minimize interaction with higher order space harmonics during bunching because the RF phase velocity is matched approximately with electron velocity.

main accelerating structure can comprise a structure similar to waveguide buncher but without tapering (e.g., phase velocity is constant and equal or close to speed of light). This section can be configured to provide only the acceleration to the beam with no bunching effect.

Although constant impedance (e.g., same cells) structure can be used, alternatively, a constant gradient (e.g., compensated field attenuation) structure can be used to reduce the interaction of the beam with higher order modes. The main accelerating structure can be integrated with a waveguide buncher.

The example electron beam current at the target of 2.1 A of Table 1 is about a factor of eight higher than that of a conventional medical linac, which are already limited by the electron current density incident onto the target 120 (e.g., X-ray converter). However, the linac system 110 of certain implementations described herein utilizes relative short beam-on time periods (e.g., one second every 15 minutes or so). In certain implementations in which pulsed heating brings a stationary target material beyond its failure threshold, a moving and/or disposable target can be used.

Figure 2A:
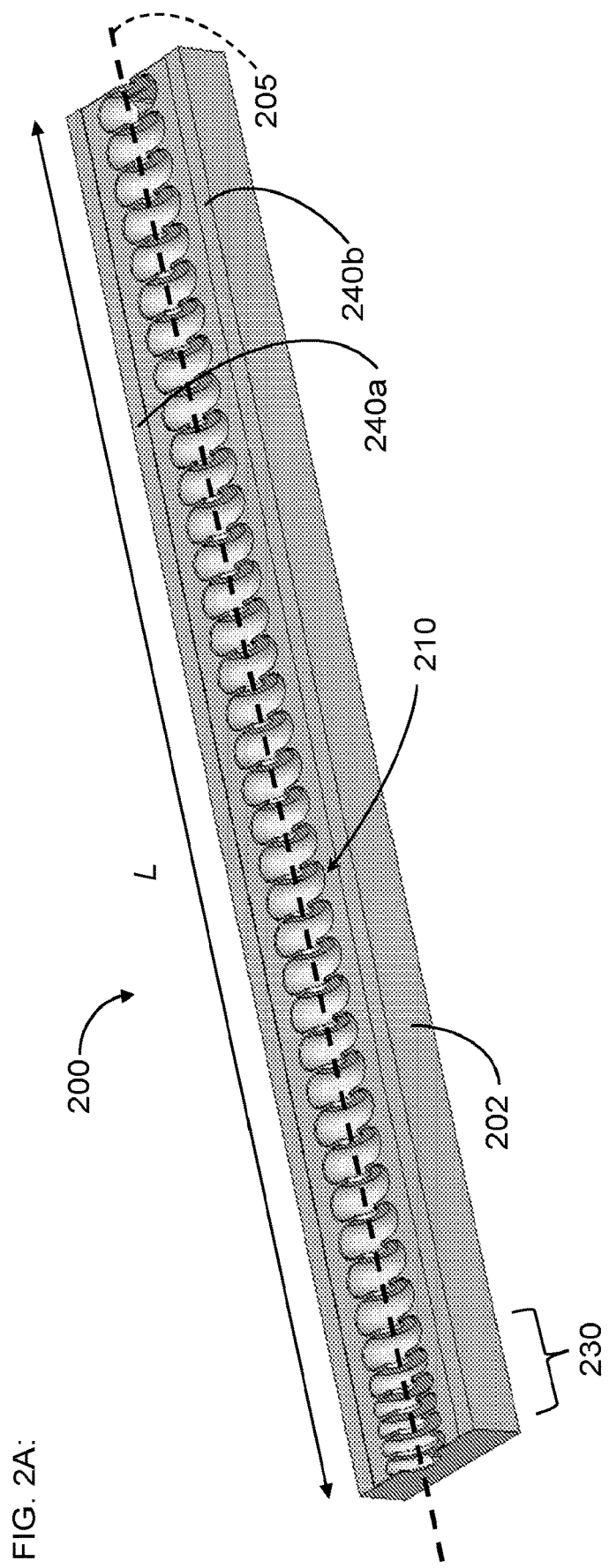
FIG. 2A schematically illustrates an isometric view of a cross-section of a first portion of an example electron accelerating structure in accordance with certain implementations described herein.
Figure 2C:
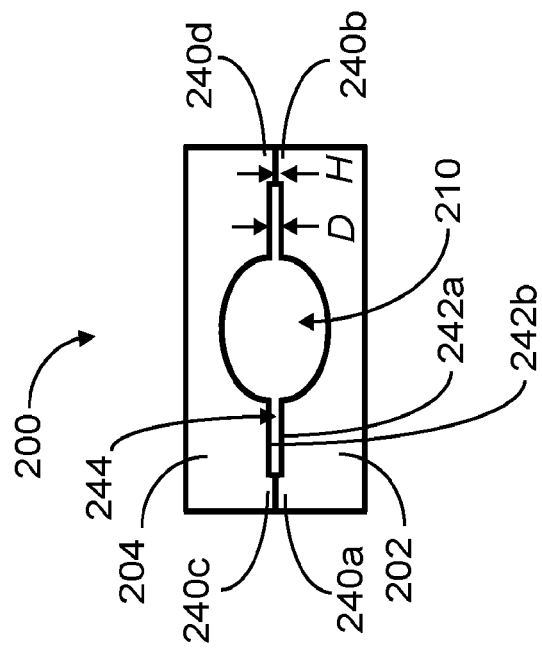
FIG. 2C schematically illustrates a cross-sectional view of the first portion of the example electron accelerating structure of FIG. 2A and a second portion of the example electron accelerating structure of FIG. 2A in a plane perpendicular to a longitudinal axis of the electron accelerating structure in accordance with certain implementations described herein.
Figure 2B:
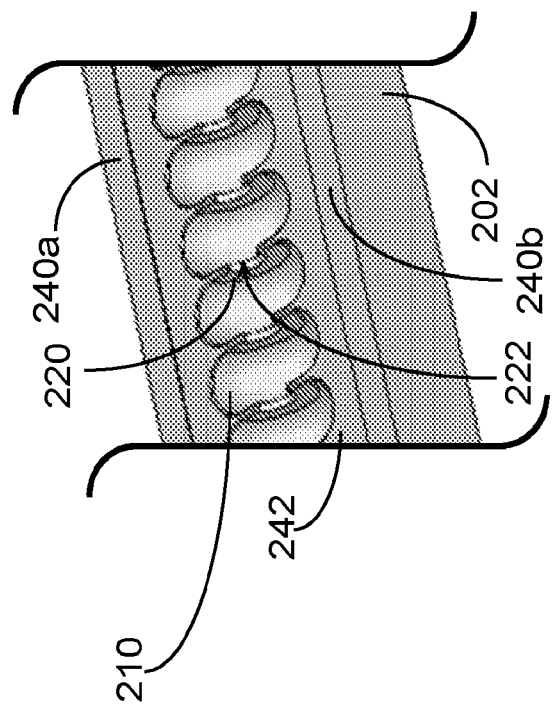
FIG. 2B schematically illustrates a closer view of a sub-portion of the first portion of the example electron accelerating structure of FIG. 2A.

FIG. 2A schematically illustrates an isometric view of a cross-section of a first portion 202 of an example electron accelerating structure 200 in accordance with certain implementations described herein. The example electron accelerating structure 200 of FIG. 2A is an electron constant gradient accelerating structure with an integrated tapered waveguide bunching section. FIG. 2B schematically illustrates a closer view of a sub-portion of the first portion 202 of the example electron accelerating structure 200 of FIG. 2A. FIG. 2C schematically illustrates a cross-sectional view of the first portion 202 of the example electron accelerating structure 200 of FIG. 2A and a second portion 204 of the example electron accelerating structure 200 of FIG. 2A in a plane perpendicular to a longitudinal axis 205 of the electron accelerating structure 200 in accordance with certain implementations described herein. The example electron accelerating structure 200 of FIGS. 2A-2B has a split constant gradient travelling wave structure designed for use in a corresponding linac system 100 and has an overall length L in a range of 0.5 m to 3.0 m (see, e.g., Int'l Appl. No. WO2018/222839, which is incorporated in its entirety by reference herein).

In certain implementations, as schematically illustrated in FIGS. 2A-2B, the electron accelerating structure 200 has a longitudinal axis 205 and comprises a plurality of cells 210 (e.g., cavities) and a plurality of cell irises 220, each having a corresponding iris aperture 222. The cell irises 220 (e.g., walls) are between adjacent cells 210 and separate the adjacent cells 210 from one another, and the iris apertures 222 (e.g., holes through the cell irises 220) are configured to allow the electrons to propagate from one cell 210 to the next, and to be accelerated along the longitudinal axis 205 of the electron accelerating structure 200. In certain implementations, the number of cells 210 can be in a range of 5 to 75 (e.g., 39 cells). At least a portion of the plurality of cells 210 can form a buncher 230, with the number of cells in the buncher 230 in a range of 1 to 25 (e.g., 9 cells).

In certain implementations, the iris apertures 222 can have a shape that is circular, ellipsoidal, race-track, rectilinear, geometric, non-geometric, or another shape. The sizes (e.g., widths; heights; diameters; in a direction perpendicular to the longitudinal axis 205) of the iris apertures 222 are different for different cells 210 along the longitudinal axis 205. For example, as schematically illustrated by FIG. 2A, beginning from a first end of the electron accelerating structure 220 (e.g., cells 210 of the buncher 230), the iris apertures 222 can be progressively smaller for each subsequent cell 210 along the longitudinal axis 205 (e.g., progressing towards a second end of the electron accelerating structure 220). In certain implementations, the sizes of the iris apertures 222 are different for different cells 210 only along a first length of the electron accelerating structure 220, and are substantially equal to one another along a remaining length of the electron accelerating structure 220 (e.g., the sizes become progressively smaller along the longitudinal axis 205, reaching an asymptotic value). In certain implementations, the cell irises 220 can be configured to control the space charge of the electron beam at the different locations of the iris apertures 222 along the electron accelerating structure 220 such that the sizes of the iris apertures 222 are larger than the electron beam size at the different locations of the iris apertures 222. In certain implementations, the cell irises 220 have cuts in one or more directions transverse to the beam axis to reduce the amplitudes of the transverse RF field harmonics. The split-structure of the electron accelerating structure 200 can have a natural gap between two halves, which can reduce the amplitudes of the transverse RF field harmonics. This reduction can be amplified by using two or more sections that are aligned by 90 degrees relative to each other, so the neighbor sections have cut planes aligned perpendicular to each other, thereby reducing the BBU effects along both transverse axes. The sizes of the iris apertures 222 can be optimized, considering the following factors: smaller apertures can provide higher accelerating gradients and power efficiency; larger aperture radii can provide better beam transmission and coupling between neighbor accelerating cells (or group velocity for the travelling wave), which define mechanical tolerances, robustness and stability of the accelerator. These factors can define a minimal possible aperture size for the accelerating section. Other aperture sizes can be chosen to provide the desired field strength profile for a given linac design.

In certain implementations, as schematically illustrated in FIG. 2C, the electron accelerating structure 200 comprises the first portion 202 and the second portion 204. The first portion 202 and the second portion 204 can be substantially similar to one another and are configured to be mounted together, one on top of the other (e.g., facing one another), with the longitudinal axis 205 between the first portion 202 and the second portion 204. Each of the cells 210 comprises a volume, a first half of the volume at least partially bounded by the first portion 202 and a second half of the volume at least partially bounded by the second portion 204.

In certain implementations, as schematically illustrated by FIGS. 2A-2C, the first portion 202 comprises at least two elongate structures 240a,b (e.g., ridges) extending along the first portion 202 (e.g., in a direction generally parallel to the longitudinal axis 205) and configured to be mechanically coupled (e.g., connected) to the second portion 204. For example, as schematically illustrated in FIG. 2C, the second portion 204 comprises two corresponding elongate structures 240c,d configured to be mechanically coupled (e.g., connected) to the respective elongate structures 240a,b of the first portion 202. In certain implementations, the elongate structures 240a,b comprise protrusions extending a height $H_1$ from a surface 242a of the first portion 202 and/or the elongate structures 240c,d comprise protrusions extending a height $H_2$ from a surface 242b of the second portion 204. The elongate structures 240a,b and/or the elongate structures 240c,d can be configured to maintain a gap 244 between the surface 242a of the first portion 202 and a corresponding surface 242b of the second portion 204, with the gap 244 having a distance D that is equal to about the summed heights $H_1$ and $H_2$ for the elongate structures 240a-d of the first portion 202 and the second portion 204 (e.g., for configurations in which elongate structures 240a,b of the first portion 202 and elongate structures 240c,d of the second portion 204 are in mechanically coupled together).

For example, in certain implementations in which the elongate structures 240a,b and the elongate structures 240c,d have substantially equal heights H from the respective surfaces 242a,b, the distance D is substantially equal to about twice the height H (D=2H). The distance D of certain implementations is in a range of 1 mm to 20 mm. In certain other implementations, only one of the first portion 202 and the second portion 204 comprises elongate structures 240, or the first portion 202 comprises one elongate structure 240 and the second portion 204 comprises another elongate structure 240. In certain implementations, the size of the gap 244 is configured to provide damping of instabilities in the electron beam due to wake fields (e.g., higher frequency RF fields) produced by other portions of the electron beam (e.g., other bunches in other cells 210).

In certain other implementations, the electron accelerating structure 220 can comprise one or more absorbers configured to dampen the higher frequency RF fields that would otherwise contribute to electron beam instabilities. The one or more absorbers can comprise a material with high RF loss properties (e.g., high loss tangent either dielectric or magnetic; silicon carbide; sendust) that covers the surface of a waveguide where the higher order (e.g., higher frequency) modes can propagate and the fundamental mode cannot (e.g., its frequency is below cut-off frequency of the damping waveguide). This dampening can be achieved by either introducing RF couplers that are configured to only couple to higher frequency modes, or by adding the absorbent materials in the drift-tubes between accelerating sections (e.g., with the diameters configured to provide cut-off frequencies beyond the fundamental accelerating mode but below the frequency of higher order modes).

In certain implementations, the interior region of the at least one electron accelerating structure 200 through which the electron beam propagates is maintained at vacuum pressures (e.g., less than 1 Torr) to reduce scattering of the electrons out of the electron beam due to interactions with gas atoms/molecules. In certain implementations, to reduce such scattering, the region traversed by the electron beam 112 while propagating to the target 120 (e.g., external to the at least one electron accelerating structure 200 and/or the linac system 110) is also under vacuum, such that the target 120 is either wholly within the same vacuum as the interior region of the at least one electron accelerating structure 200 or the target 120 comprises a portion of a barrier (e.g., wall) separating the interior region under vacuum from the surrounding region (e.g., at ambient pressure). As a result, changing or replacing the target 120 in such implementations can result in "breaking vacuum" (e.g., having at least a portion of the region under vacuum opened to ambient pressure, changing or replacing the target 120, and then pumping the region back to vacuum conditions).

For implementations in which the target 120 is contemplated to be changed or replaced often or with some regularity (e.g., for a disposable, removable, and/or replaceable target), the process of "breaking vacuum" can be unwieldy. For example, for certain implementations in which generation of a single X-ray pulse is expected to result in significant damage to the target 120 (e.g., caused by being impinged by an electron beam 112 with a high peak current), it can be desirable to have the target 120 decoupled from the region under vacuum, thereby having the electron beam 112 propagate through a region under ambient pressure.

In certain such implementations, the linac system 110 comprises at least one defocusing magnet, an electron beam window, and at least one focusing magnet. The at least one defocusing magnet (e.g., quadrupole magnet) is configured to defocus at least a portion of the electron beam 112 from the at least one electron accelerating structure 200 while the portion of the electron beam 112 is within a first region under vacuum. The electron beam window is between the first region under vacuum and a second region at ambient pressure (e.g., the electron beam window comprises a portion of the barrier or wall separating the first region from the second region). The electron beam window is configured to be impinged by the defocused portion of the electron beam 112 and to have at least a sub-portion (e.g., at least 90%) of the defocused portion of the electron beam 112 propagate through the electron beam window to the second region (e.g., the small sub-portion that does not propagate through to the second region can deposit some energy, causing the structure to heat up). The at least one focusing magnet is configured to focus (e.g., re-focus) the sub-portion of the defocused portion of the electron beam 112 onto the target 120. In certain implementations, the target 120 can be outside the rotating gantry and configured as a ring of material surrounding the patient.

In certain implementations, the target 120 can be in vacuum, and can be configured to be translated or rotated within the vacuum (e.g., the target 120 can be on a movable stage). In certain implementations, the system 100 comprises a vacuum system configured to allow replacement of the target 120 without breaking the main vacuum (e.g., the vacuum of the linac system 110 and/or the at least one electron accelerating structure 200). For example, the system 100 can comprise two or more portions of vacuum (e.g., vacuum chambers) with one or more vacuum seals between the portions of vacuum, the one or more vacuum seals configured to be repeatedly and reversibly opened and closed such that the portions of vacuum can be separated from one other. For example, to remove a target 120, a translation mechanism (e.g., mechanical arm) can be translated from an exterior chamber to an interior chamber, can be affixed (e.g., automatically or under user control) to the target 120 in the interior chamber, and can then be translated back to move the target 120 into the exterior chamber. The interior and exterior chambers can then be sealed from one another by closing the vacuum seal between the interior and exterior chambers, the exterior chamber can be vented, and the target 120 removed from the exterior chamber and replaced with a new target 120. The exterior chamber can then be pumped down, the vacuum seal between interior and exterior chambers can be opened, and the translation mechanism can be translated to install the new target 120 within the interior chamber. In certain implementations, multiple targets can be located in the exterior chamber and the translation mechanism can be configured to access each of the multiple targets to replace the active target multiple times without breaking vacuum each time. In certain implementations, each of these steps for the replacement of the target can be performed by electromechanical devices and can be automated.

Regardless of whether the target 120 is in vacuum or out of vacuum, the target 120 can be moved during the time that the electron beam 112 impinges upon the target 120 to spread out the thermal load imparted by the electron beam 112 over a wider area of the target 120. For example, such motion can comprise a rotation with an axis of rotation that is substantially parallel with, but offset from, the electron beam 112, or a translation of an extended target (e.g., ribbon) through the electron beam 112. In either of these examples, the moving target assembly can also be replaced in between treatments to avoid future failure.

In certain implementations, the system 100 comprises one or more magnets within a rotating gantry, and mechanical stresses during rotation can cause motion of the magnets with respect to the electron beam 112. Such motion can cause motion of the electron beam 112 at a point downstream, such as at the target 120. For radiation therapy, precise alignment of the electron beam 112 (e.g., the electron beam spot on the X-ray target 120) with subsequent collimators and the patient is highly desirable. Therefore, certain implementations described herein comprise an electron beam correction system configured to quickly adjust a position of the electron beam spot location relative to the X-ray target 120. For example, the electron beam correction system can comprise a beam position monitor configured to measure an offset (e.g., at a point upstream from the target 120) between the electron beam position and a desired position of the electron beam, and one or more steering magnets configured to quickly adjust the electron beam position in response to adjustments of one or more electrical currents of the one or more steering magnets, the adjustments based on calculations of desired corrections determined from signals from the beam position monitor.

In certain implementations, the X-ray generation system 100 further comprises at least one collimator assembly configured to receive the X-ray beam 122 emitted from the target 120 and to reduce a spatial extent of the X-ray beam 122 in the transverse direction (e.g., to reduce the size of the X-ray beam 122 in a direction perpendicular to a propagation direction of the X-ray beam 122). In certain implementations, the X-ray beam 122 emitted from the target 120 has a natural, sharply-peaked yet broad transverse distribution and the at least one collimator assembly is configured to shape the X-ray beam 122 transversely. For example, the at least one collimator assembly can comprise one or more elements that are substantially opaque to the X-rays generated by the target 120 and are configured to bound an aperture that is substantially transmissive to the X-rays generated by the target 120. For example, the at least one collimator assembly can comprise one or more structures comprising a material (e.g., lead; tungsten) through which the X-rays do not propagate (e.g., are blocked or absorbed), and each of the one or more structures can have an edge which at least partially bounds an aperture region through which the X-rays can propagate. The at least one collimator assembly can be positioned such that a central portion of the X-ray beam 122 propagates through the aperture region and past the at least one collimator assembly while a non-central portion of the X-ray beam 122 is substantially blocked by the at least one collimator assembly.

In certain implementations, the one or more structures are configured to be controllably moved relative to the X-ray beam 122 such that a size and/or shape of the aperture region is controllably adjusted (e.g., optimized). For example, in three-dimensional (3D) conformal RT, the incident direction of the X-ray beam 122 is varied relative to the patient to irradiate the target tissue (e.g., tumor having an irregular shape) from multiple angles. The one or more structures of the at least one collimator assembly for such 3D conformal RT can be controllably moved relative to the X-ray beam 122 (e.g., controlled by specialized software that determines the correct aperture shape from each beam angle) such that the shape of the portion of the X-ray beam 122 propagating through the aperture is optimized (e.g., substantially matches the shape of the tumor from each direction).

Beam Delivery and Intensity Modulation

In RT, the radiation is delivered to the target tissue from many angles in an arc around the patient. The target tissue (e.g., tumor) is positioned on the axis around which the linac rotates, thereby irradiating the target tissue from multiple angles, and the delivered radiation mostly adds up at the target tissue on the axis, while being more spread out in the surrounding tissues that are off the axis.

Certain implementations described herein are configured to deliver FLASH RT dosages (e.g., within less than one second) from angles all around the patient. For example, at least a portion of the linac system 110 (e.g., the at least one electron accelerating structure 200) can be configured to rotate around the patient with a rotation rate greater than 60 rpm (e.g., rotating by an entire revolution or 360 degrees in less than one second; rotation rate in a range of 20 revolutions per minute to 200 revolutions per minute). For example, an RT system developed by Reflexion Medical Inc. of Hayward, CA comprises a linac mounted on a 60 rpm gantry, and other medical CT systems commonly operate at up to 180 rpm.

In certain implementations, the X-ray generation system 100 comprises a plurality of linac systems 110 mounted on a gantry (e.g., fixed or controllably rotatable) and spaced from one another and distributed around a region 310 configured to receive the patient (e.g., to reduce the dose provided by any one linac system 110; to reduce the gantry speed for delivering the FLASH RT dosage at various angles). In certain other implementations, the X-ray generation system 100 comprises a single linac system 110. FIGS. 3A-3D schematically illustrate example X-ray generation systems 100 comprising a single linac system 110 in accordance with certain implementations described herein.

Figure 3A:
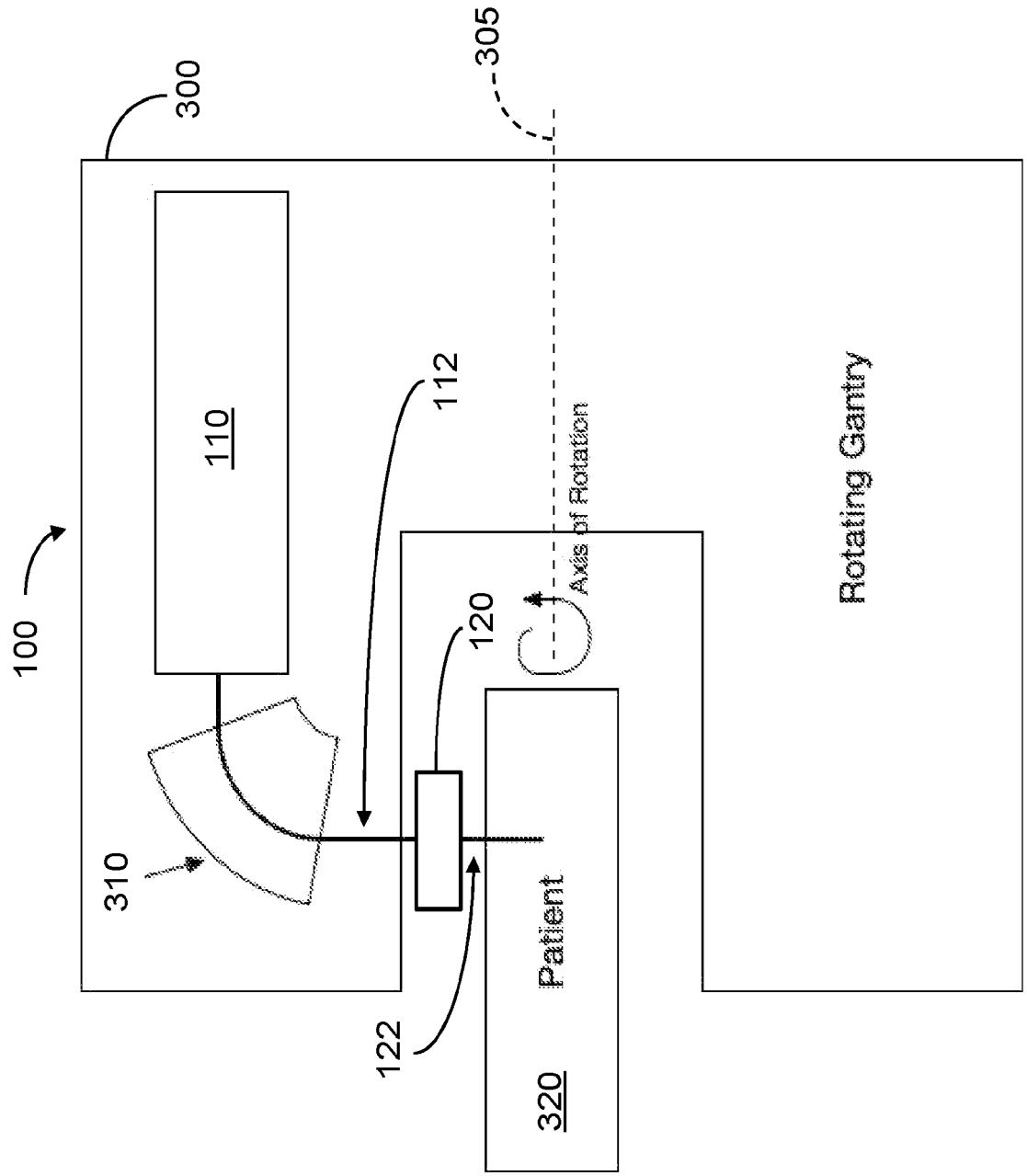
FIGS. 3A-3E schematically illustrate example X-ray generation systems comprising a single linac system in accordance with certain implementations described herein.
Figure 3B:
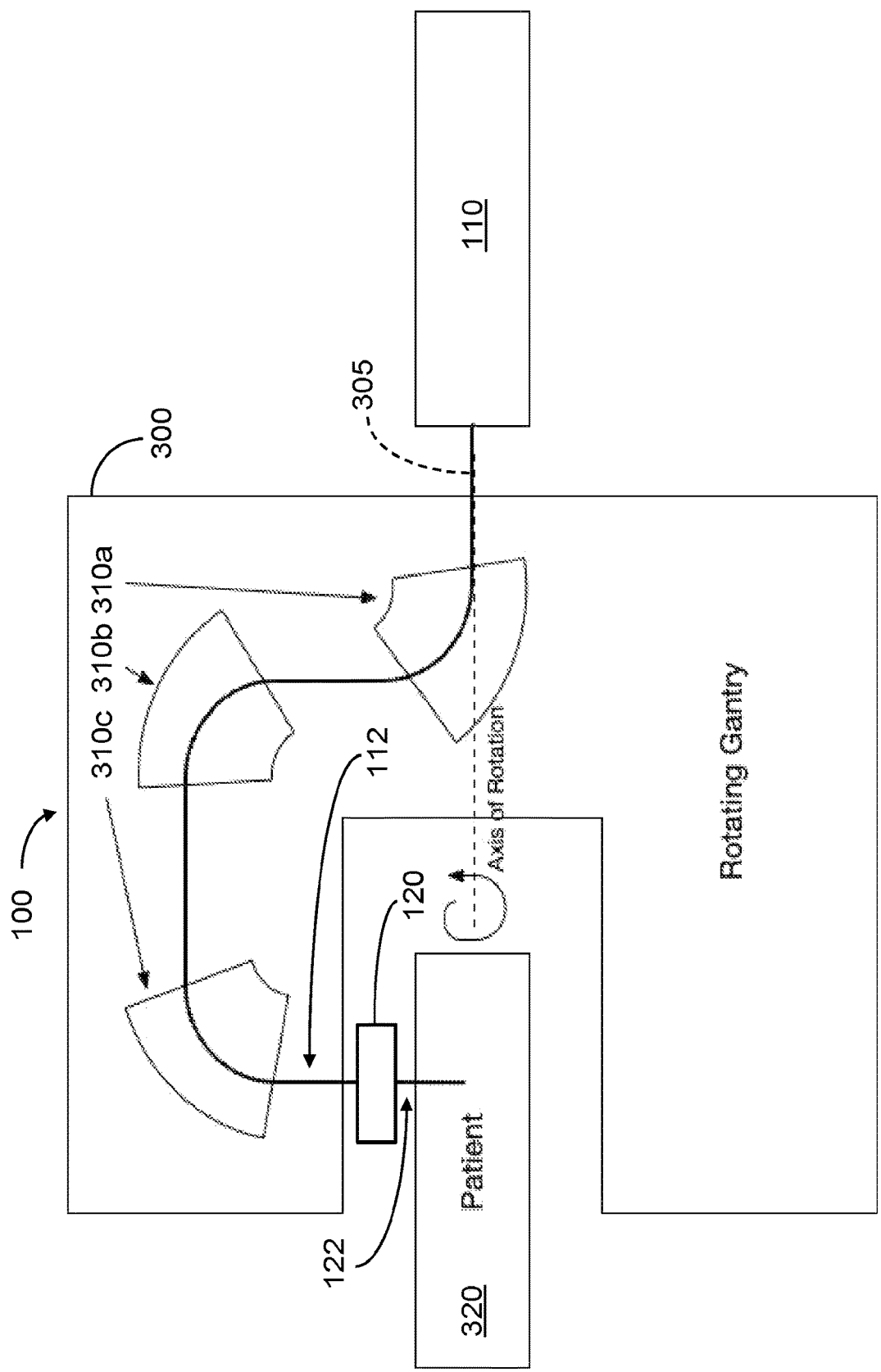

FIGS. 3A-3B schematically illustrate two example X-ray generation systems 100 comprising a controllably rotatable gantry 300 having a rotation axis 305 about which a rotatable portion of the gantry 300 is configured to rotate in accordance with certain implementations described herein. In FIG. 3A, the single linac system 110 of the example X-ray generation system 100 is mounted in or on the rotatable portion of the gantry 300, and an electron optics sub-system 310 (e.g., at least one bending magnet) is mounted in or on the rotatable portion of the gantry 300. For example, as shown in FIG. 3A, the electron optics sub-system 310 can comprise a focusing and/or bending magnet configured to direct the electron beam 112 from propagating in a first direction from the linac system 110 to propagating in a second direction (e.g., substantially perpendicular to the first direction) towards the target 120.

In FIG. 3B, the single linac system 110 of the example X-ray generation system 100 is mounted outside or off the rotatable portion of the gantry 300, the electron optics sub-system 310 (e.g., a plurality of focusing and/or bending magnets) is mounted in or on the rotatable portion of the gantry 300, and the single linac system 110 is operationally coupled to the electron optics sub-system 310 by a rotary vacuum joint. For example, as shown in FIG. 3B, the electron optics sub-system 310 can comprise three focusing and/or bending magnets 310a-c each configured to direct the electron beam 112 from propagating in a first direction to propagating in a second direction (e.g., substantially perpendicular to the first direction). As shown in FIG. 3B, a first magnet 310a is configured to deflect the electron beam 112 from the linac system 110 (e.g., by about 90 degrees), a second magnet 310b is configured to deflect the electron beam 112 from the first magnet 310a (e.g., by about 90 degrees), and a third magnet 310c is configured to deflect the electron beam 112 from the second magnet 310b (e.g., by about 90 degrees) to propagate towards the target 120. At each position of the rotatable portion of the gantry 300, the X-rays 122 from the target 120 impinge the same target tissue of the patient in the region 320 from different angles or directions.

Certain implementations described herein take advantage of the inherent electron beam energy spread and the fact that lower energy beams deflect greater than do higher energy beams by using path length focusing to longitudinally compress the beam for higher peak currents. Certain implementations described herein comprise electron beam collimators at optimal locations within the magnetic transport where the beam energy is determined (e.g., utilizing the inherent electron beam energy spread) to be correlated to a transverse position to reduce the electron beam energy tails, thereby reducing stray electrons.

In certain implementations, the magnet system is configured to take into account point-to-point focusing effects and energy/transverse position dependent transverse focusing effects to reduce beam spot size or increase beam spot size to manage thermal effects on the target. For example. dipole magnet entry angles and entry edge features can be shaped to accomplish such changes of the beam spot size. The entry angles can affect the first order focusing more significantly, while the entry edge shaping (e.g., chamfers, radii or more complex shapes) can provide a greater volume of high quality field within the magnet, while reducing the size and thus weight of the magnet. Magnet pole faces can also be "shaped" with bumps and features to provide a greater volume of high quality field within the magnet with a pole face size.

Certain implementations described herein are configured to be operated in a low duty cycle, such that the thermal management of the magnets is simplified as thermal equilibrium, ohmic losses, and voltage runaway are extremely sensitive the average power of the system. For example, a system configured to be on for 5 minutes and off for 55 minutes can handle more power than can a system designed to be continually on for 55 minutes. The low duty cycle of certain implementations can allow smaller coil geometries to be used and can reduce overall system weight.

Certain implementations described herein comprise high permeability magnet steels (e.g., pure iron, vanadium permendur, very low carbon steel) configured to increase the internal field handling limits of the steel yoke and placed in appropriate locations to reduce the size of the magnet yoke. Certain implementations described herein comprise hybrid magnet construction topologies with a mix of steel and permanent magnets with electrical coils configured to significantly reduce the size of the magnets and the system power draw. By reducing the overall magnetic transport weight as described herein, certain implementations can advantageously reduce support superstructure centrifugal loads thus making it easier to develop balanced mechanical rotation systems that are less susceptible to misalignment during high speed rotation. Further weight reduction in the beam transport are achieved by certain implementations that comprise passive vacuum pumping elements, (e.g., getters) configured to absorb vacuum gases thereby reducing the number and size of active pumping elements such as ion pumps.

Figure 3C:
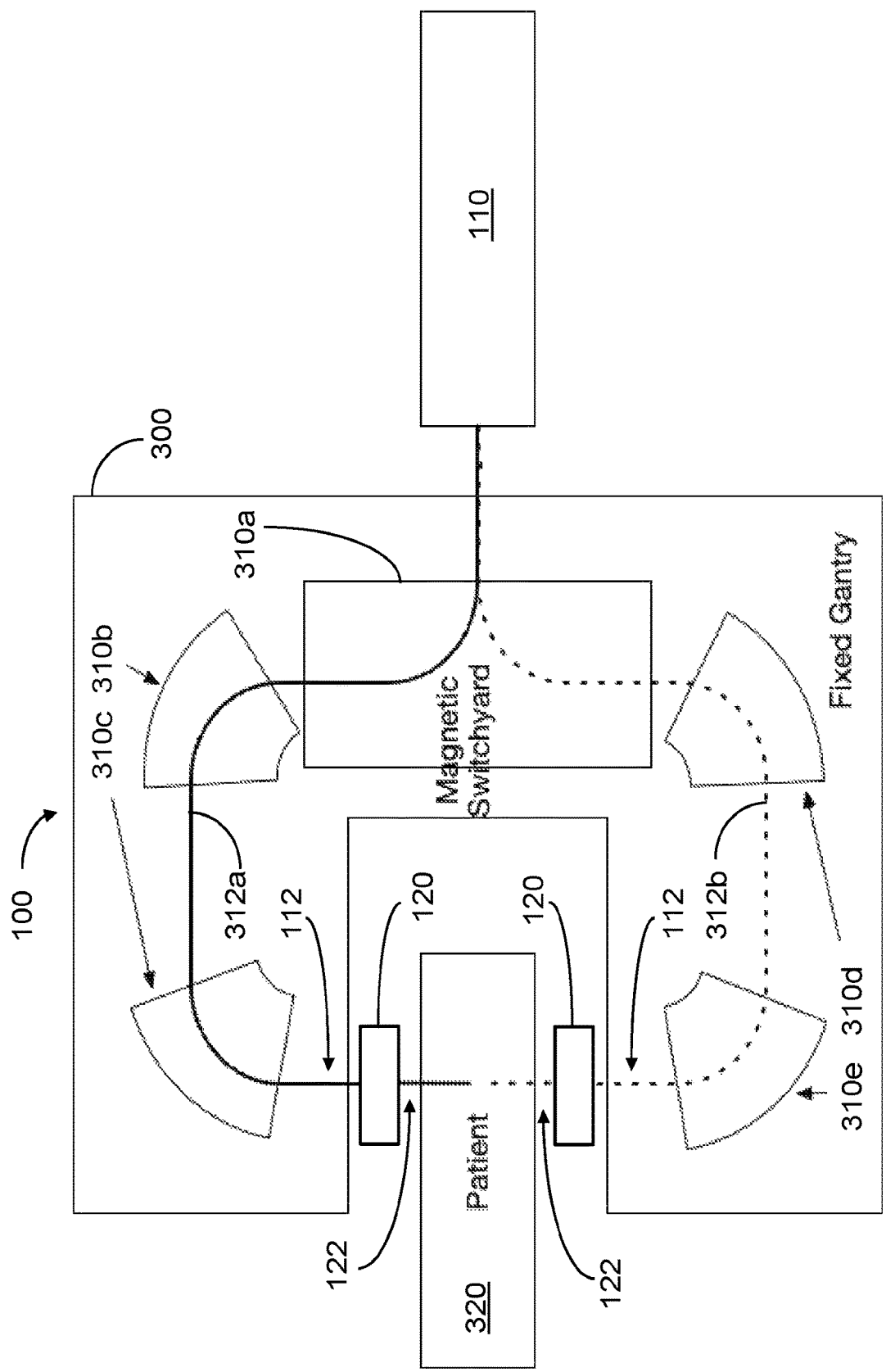

FIG. 3C schematically illustrates an example X-ray generation system 100 comprising a fixed gantry 300 in accordance with certain implementations described herein. In FIG. 3C, the single linac system 110 of the example X-ray generation system 100 is mounted outside or off the gantry 300, and the electron optics sub-system 310 (e.g., a plurality of focusing and/or bending magnets) is mounted in or on the gantry 300. For example, as shown in FIG. 3C, the electron optics sub-system 310 can comprise a controllably switchable magnet system 310*a* (e.g., a magnetic switchyard; comprising pulsed magnets) configured to direct the electron beam 112 from propagating in a first direction from the linac system 110 to propagating in a selected one of a plurality of second directions (e.g., substantially perpendicular to the first direction). The electron optics sub-system 310 can further comprise a plurality of beam paths 312, each beam path 312 comprising at least one focusing and/or bending magnet 310*b-e*. For example, as shown in FIG. 3B, a first beam path 312*a* comprises a first magnet 310*b* configured to deflect the electron beam 112 from the magnet system 310*a* (e.g., by about 90 degrees) and a second magnet 310*c* is configured to deflect the electron beam 112 from the first magnet 310*b* (e.g., by about 90 degrees) to propagate towards the target 120. In addition, a second beam path 312*b* (e.g., at a second azimuthal position relative to the patient different from a first azimuthal position of the first beam path 312*a*) comprises a third magnet 310*c* configured to deflect the electron beam 112 from the magnet system 310*a* (e.g., by about 90 degrees) and a fourth magnet 310*d* is configured to deflect the electron beam 112 from the third magnet 310*c* (e.g., by about 90 degrees) to propagate towards the target 120. In this way, certain implementations described herein utilize the controllably switchable magnet system 310*a* to switch the electron beam 112 to different beam paths 132 at different azimuthal positions around the patient. The X-rays 122 from the target 120 along each of the beam paths 312 impinge the same target tissue of the patient in the region 320 from different angles or directions.

Figure 3D:
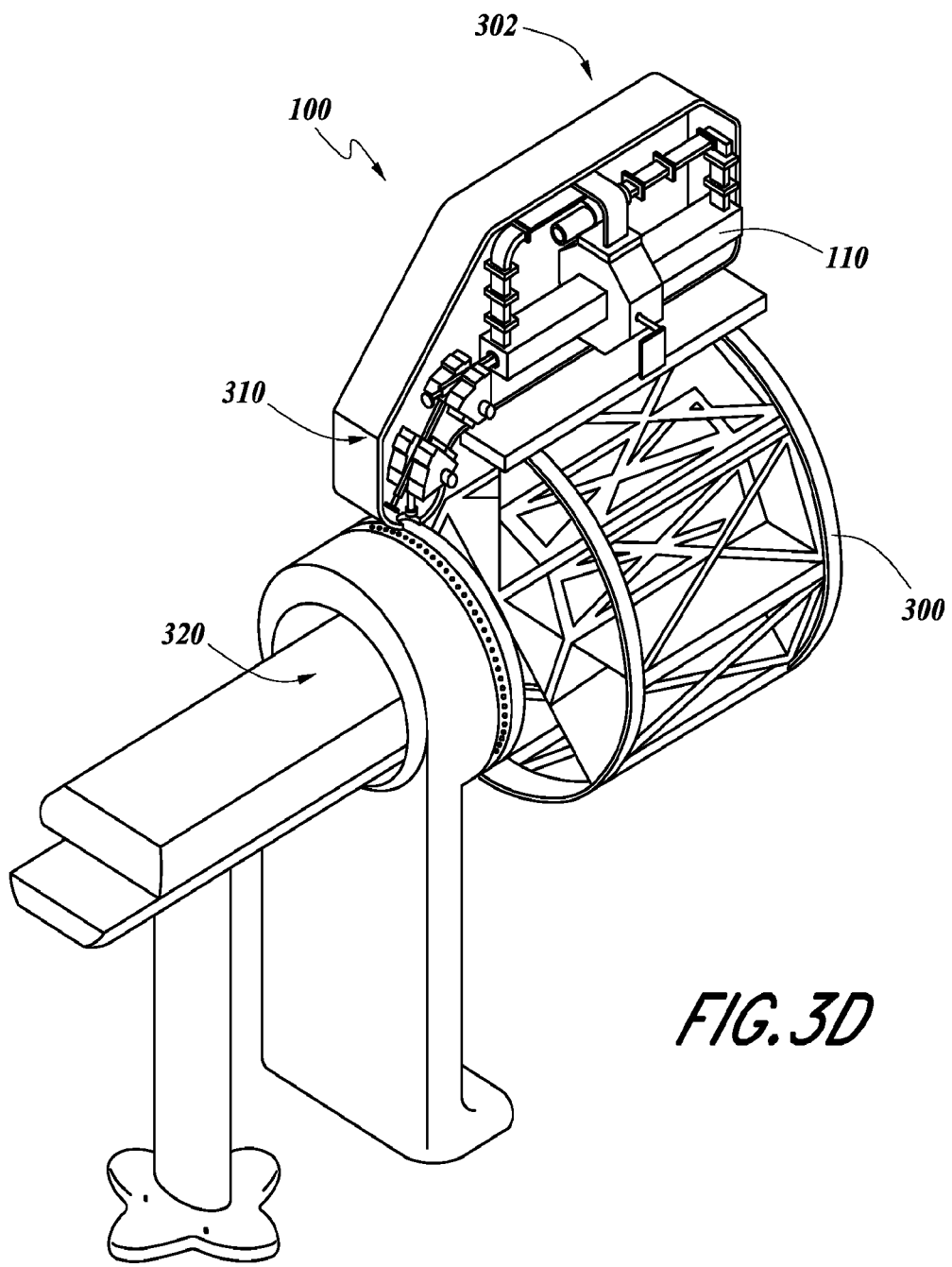

FIG. 3D schematically illustrates an example X-ray generation system 100 comprising a gantry 300 having a controllably rotatable portion in accordance with certain implementations described herein. The controllably rotatable portion of the gantry 300 is configured to be rotated about the patient in the region 320. The single linac system 110 and the electron optics sub-system 310 (e.g., comprising two bending magnets) of the example X-ray generation system 100 are mounted on the rotatable portion of the gantry 300. At each position of the rotatable portion of the gantry 300, the X-rays 122 from the target 120 (not shown in FIG. 3D) impinge the same target tissue of the patient in the region 320 from different angles or directions.

Figure 3E:
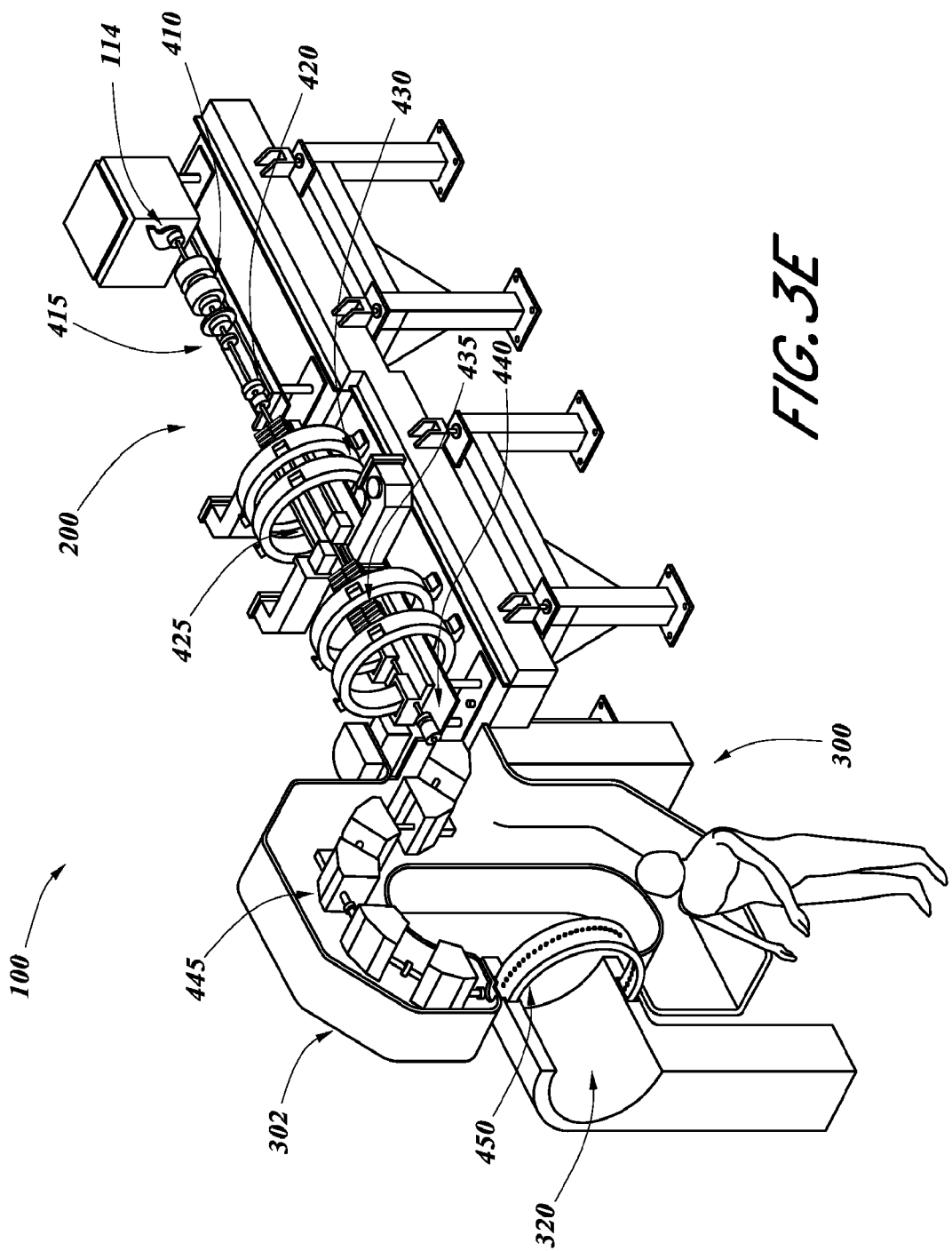

FIG. 3E schematically illustrates a partial cut-away view of another example X-ray generation system 100 comprising a gantry 300 having a controllably rotatable portion 302 in accordance with certain implementations described herein. The system 100 of FIG. 3E comprises a linear accelerator system 110 comprising an electron source 114 and at least one electron accelerating structure 200. The electron accelerating structure 200 comprises quadrupole magnets 410, pre-buncher 415, chopper 420, tapered-phase-velocity (TPV) accelerator 425, solenoid magnets 430, speed-of-light (SOL) accelerator 435, vacuum rotary coupler 440, bending magnets 445, and multi-leaf collimator (MLC) 450. The In certain implementations, the MLC 450 is configured to be fixed relative to the patient, while in certain other implementations, the MLC 450 is configured to rotate about the patient in a direction opposite to the rotational direction of the controllably rotatable portion 302 of the gantry 300.

Figure 3F:
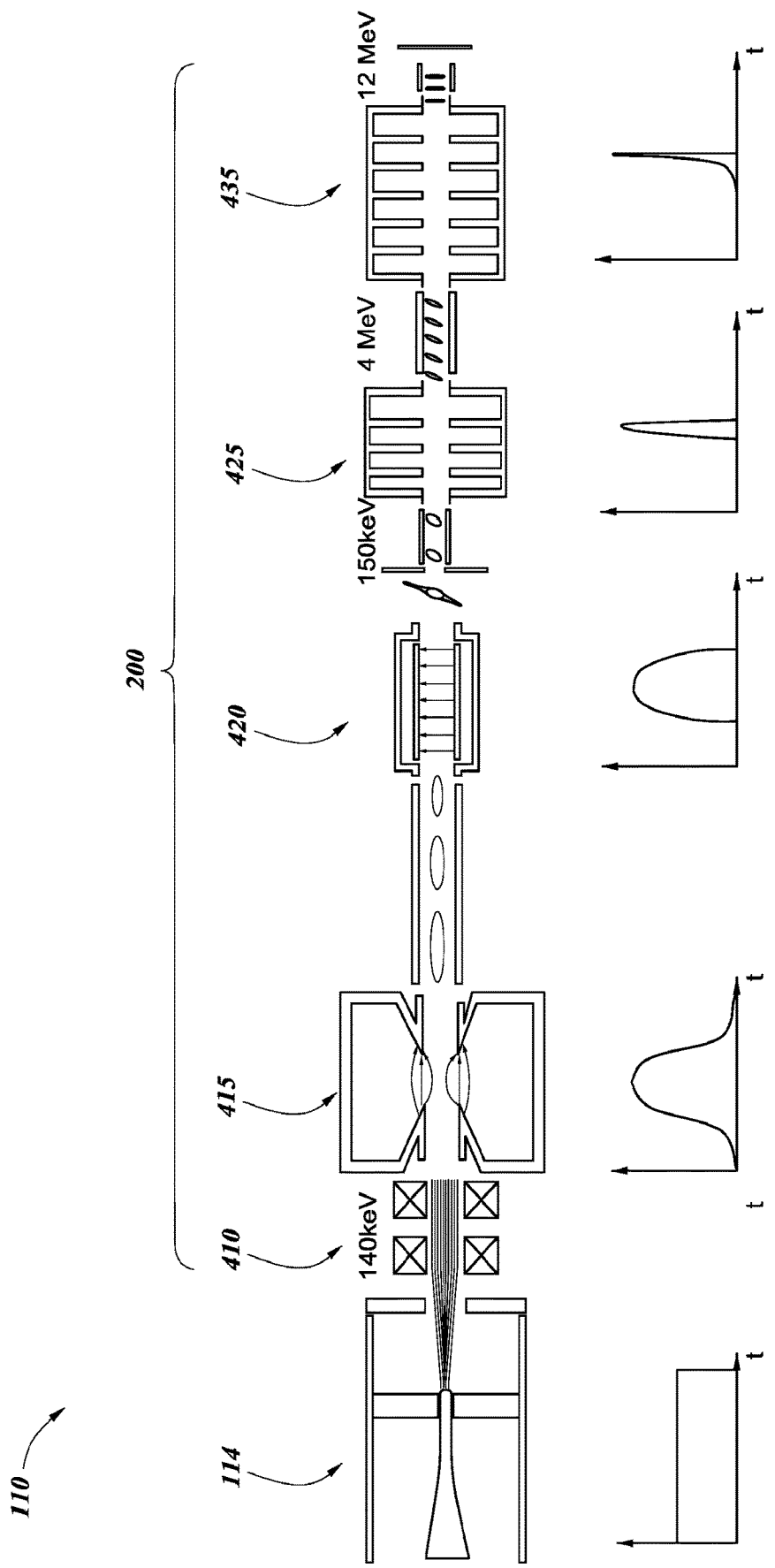
FIG. 3F schematically illustrates an example linear accelerator system of FIG. 3E with an electron beam longitudinal profile development in accordance with certain implementations described herein.

FIG. 3F schematically illustrates an example linear accelerator system 110 of FIG. 3E with an electron beam longitudinal profile development in accordance with certain implementations described herein. An electron beam from the electron source 114 (e.g., thermionic DC Pierce geometry electron gun generating 140 keV electrons) can have at least 6A such that the electron beam outputted from the electron accelerating structure 200 has at least 1.5 A after losses in the electron accelerating structure 200. In certain implementations, the quadrupole magnets 410 are configured to defocus the electron beam emerging from the electron source 114 to maintain an electron beam radius less than or equal to 1 cm (e.g., to avoid second-order lens aberrations). The electron beam subsequently propagates through a plurality of bunching and focusing elements configured to capture portions of the DC electron beam from the quadrupole magnets 410 into RF accelerating potential "buckets." For example, as schematically illustrated in FIG. 3F, a pre-buncher 415 (e.g., single-cell bunching cavity) and a chopper 420, both operating at a harmonic FR frequency (e.g., 1 GHz), form a bunched electron beam that is injected into the traveling-wave TPV accelerator 425 (e.g., having a length approximately equal to 50 cm) and that is accelerated (e.g., from 4 MeV to 12 MeV) by the traveling-wave SOL accelerator 435 (e.g., having a length approximately equal to 50 cm). Solenoid magnets 430 positioned between the TPV accelerator 425 and the SOL accelerator 435 can be configured to mitigate the repulsive space charge force.

In certain implementations, the X-ray generation system 100 provides significantly higher dose rates than are used by conventional medical linacs. For example, while conventional medical linacs produce average electron beam powers of around 1 kW, certain implementations described herein provide average electron beam powers on the order of 100 kW. For a dose conversion factor of $6.5 \times 10^4$ cGy/min/mA at 12 MeV, the beam power for achieving 100 Gy/s at 1 m can be 111 kW. Furthermore, in contrast to industrial accelerators that are configured to provide such high average electron beam powers in a factory setting with very little downtime (e.g., 24 hours per day, seven days a week)(see, e.g., National Council on Radiation Protection and Measurements, "Radiation protection design guidelines for 0.1-100 MeV particle accelerator facilities: recommendations of the National Council on Radiation Protection and Measurements," NCRP report no. 51, Washington: The Council. vii, 159 p. (1977)), in certain implementations described herein, the electron beam is only on for a brief time (e.g., on the order of 1 second every 15 minutes), which significantly relaxes operational parameters for the various components of the system (e.g., power supplies; cooling systems). As an example, electron beam parameters of the CLIC drive beam injector are 4 MeV, 4.2 A peak, 0.007 duty cycle, resulting in 118 kW average beam power (see, e.g., M. Aicheler, et al., "A Multi-TeV Linear Collider Based on CLIC Technology: CLIC Conceptual Design Report," CERN-2012-007 (2012); S. Döber, "High-efficiency L-band klystron development for the CLIC drive beam. in CLIC workshop," CERN, Geneva Switzerland (2016); M. C. Vozenin, et al., "Biological Benefits of Ultra-high Dose Rate FLASH Radiotherapy: Sleeping Beauty Awoken," Clin. Oncol. (R. Coll. Radiol.), Vol. 31(7), p. 407-415 (2019); J. Bourhis, et al., "Clinical translation of FLASH radiotherapy: Why and how?," Radiother. Oncol. Vol. 139: p. 11-17 (2019)).

In certain implementations, the X-ray generation system 100 is configured to deliver X-ray doses to the patient from about 100 different azimuthal angles around the patient (e.g., with the linac system 100 pulsing at about 100 Hz for a time duration of one second as the X-ray beam 112 is cycled (e.g., rotated) through one revolution of the azimuthal angle about the patient. In certain implementations in which the RT treatments are planned in advance, the at least one collimator assembly can be configured to provide the X-ray beam 112 with an optimized shape from each of the beam angles. For example, the collimator assembly can comprise Cerrobend collimators or 3D-printed plastic enclosures filled with an X-ray absorbing material (e.g., lead shot; tungsten powder) (see, e.g., L. Skinner et al., "Tungsten filled 3D printed field shaping devices for electron beam radiation therapy," PLoS ONE 14(6):e0217757, https://doi.org/10.1371/journal-.pone.0217757 (2019)). The shape of the collimator assembly can appear as a ring within the gantry 300.

Figure 4:
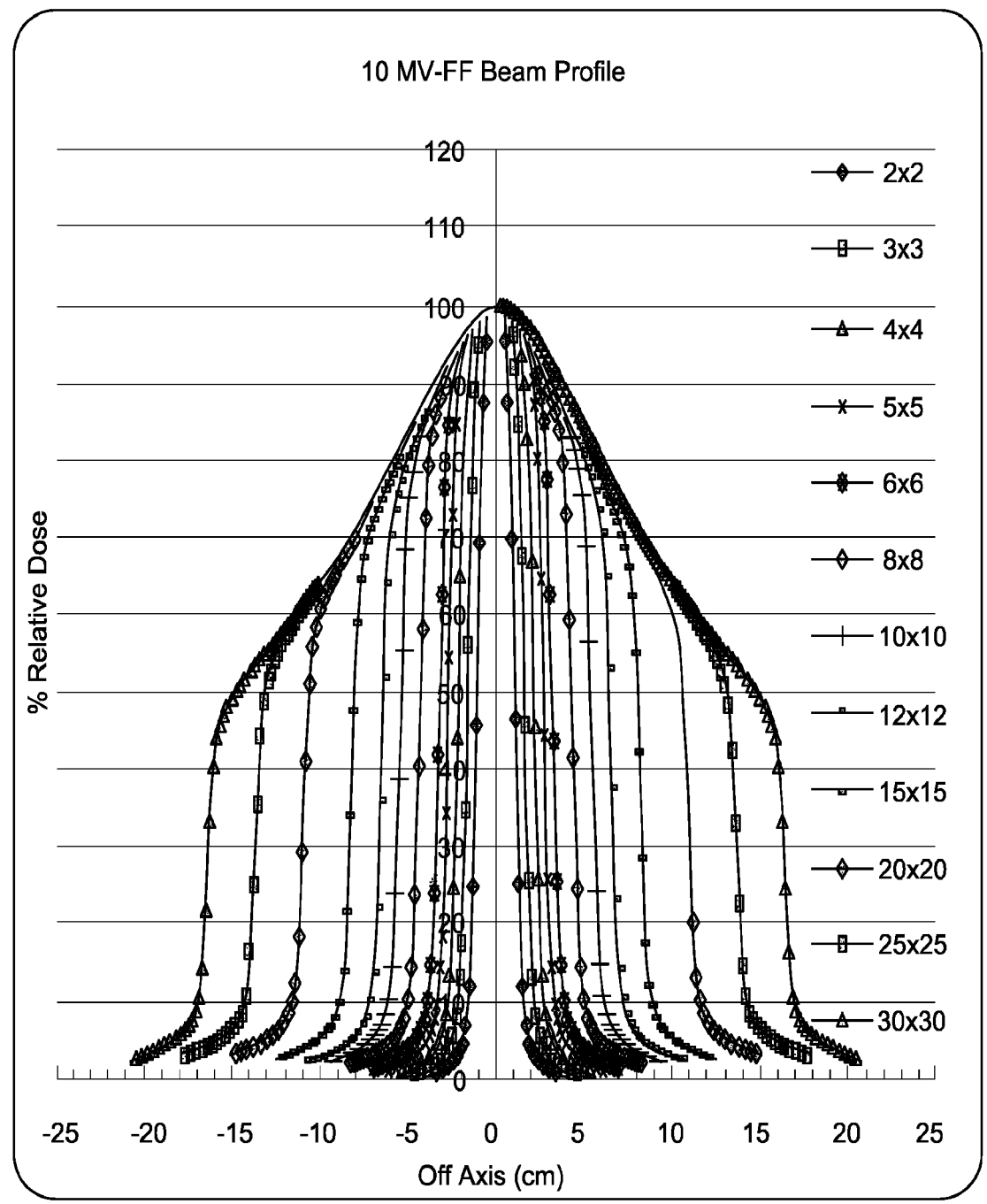
FIG. 4 is a plot of the shape of a 10 MeV X-ray beam in the transverse direction for different sizes of the aperture of an adjustable collimator assembly in accordance with certain implementations described herein.

FIG. 4 is a plot of the shape of a 10 MeV X-ray beam 122 in the transverse direction for different sizes of the aperture of an adjustable collimator assembly in accordance with certain implementations described herein. As shown in FIG. 4, the intensity (e.g., % relative dose) of the X-ray beam 122 along the transverse direction (e.g., as a function of the off axis position) can be controllably varied by adjusting a size of the aperture of the collimator assembly (e.g., from 2×2 cm 2 to 30×30 cm 2) (see, e.g., R. Shende et al., "Commissioning of TrueBeam™ Medical Linear Accelerator: Quantitative and Qualitative Dosimetric Analysis and Comparison of Flattening Filter (FF) and Flattening Filter Free (FFF) Beam," Int'l J. Med. Phys., Clinical Eng. And Rad. Oncol., 5, 51-69 (2015)).

In certain implementations, the X-ray generation system 100 is configured to perform Intensity Modulated Radiation Therapy (IMRT), which can provide even greater conformality of the X-ray beam 112 to the target tissue by utilizing a dynamic collimator to modulate the intensity of the X-ray beam 112 across a field on a pixel-by-pixel basis. For example, in certain implementations described herein, the collimator assembly can comprise a plurality of dynamically adjustable planar structures (e.g., leaves of a multi-leaf collimator or MLC). In certain implementations, the at least one collimator assembly is detached from the rotatable gantry 300 (e.g., such that the gantry 300 is controllably rotated without affecting a position or orientation of the at least one collimator assembly relative to the patient).

In certain implementations, the X-ray generation system 100 has a substantially circularly symmetric geometry (e.g., compatible with 3D imaging systems) and is configured to provide fast, precise, real-time alignment and delivery of the X-ray doses. In certain implementations in which the X-ray beam is incident on the patient at a small angle of incidence (e.g., within a range of 0 degrees to 30 degrees from a direction perpendicular to the patient's body), so that an imaging system (e.g., computed tomography (CT) scanner; magnetic resonance imaging (MRI) system; positron emission tomography (PET) imaging system) can be placed directly around the tumor site and used in conjunction with the X-ray generation system 100.

The invention has been described in several non-limiting implementations. It is to be understood that the implementations are not mutually exclusive, and elements described in connection with one implementation may be combined with, rearranged, or eliminated from, other implementations in suitable ways to accomplish desired design objectives. No single feature or group of features is necessary or required for each implementation.

For purposes of summarizing the present invention, certain aspects, advantages and novel features of the present invention are described herein. It is to be understood, however, that not necessarily all such advantages may be achieved in accordance with any particular implementation. Thus, the present invention may be embodied or carried out in a manner that achieves one or more advantages without necessarily achieving other advantages as may be taught or suggested herein.

As used herein any reference to "one implementation" or "some implementations" or "an implementation" means that a particular element, feature, structure, or characteristic described in connection with the implementation is included in at least one implementation. The appearances of the phrase "in one implementation" in various places in the specification are not necessarily all referring to the same implementation. Conditional language used herein, such as, among others, "can," "could," "might," "may," "e.g.," and the like, unless specifically stated otherwise, or otherwise understood within the context as used, is generally intended to convey that certain implementations include, while other implementations do not include, certain features, elements and/or steps. In addition, the articles "a" or "an" or "the" as used in this application and the appended claims are to be construed to mean "one or more" or "at least one" unless specified otherwise.

As used herein, the terms "comprises," "comprising," "includes," "including," "has," "having" or any other variation thereof, are open-ended terms and intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), or both A and B are true (or present). As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain implementations require at least one of X, at least one of Y, and at least one of Z to each be present.

Language of degree, as used herein, such as the terms "approximately," "about," "generally," and "substantially," represent a value, amount, or characteristic close to the stated value, amount, or characteristic that still performs a desired function or achieves a desired result. For example, the terms "approximately," "about," "generally," and "substantially" may refer to an amount that is within ±10% of, within ±5% of, within ±2% of, within ±1% of, or within ±0.1% of the stated amount. As another example, the terms "generally parallel" and "substantially parallel" refer to a value, amount, or characteristic that departs from exactly parallel by ±10 degrees, by ±5 degrees, by ±2 degrees, by ±1 degree, or by ±0.1 degree, and the terms "generally perpendicular" and "substantially perpendicular" refer to a value, amount, or characteristic that departs from exactly perpendicular by ±10 degrees, by ±5 degrees, by ±2 degrees, by ±1 degree, or by ±0.1 degree.

Thus, while only certain implementations have been specifically described herein, it will be apparent that numerous modifications may be made thereto without departing from the spirit and scope of the invention. Further, acronyms are used merely to enhance the readability of the specification and claims. It should be noted that these acronyms are not intended to lessen the generality of the terms used and they should not be construed to restrict the scope of the claims to the implementations described therein.

What is claimed is:

1. An X-ray generation system configured to generate an X-ray beam configured to be delivered to a patient undergoing radiation therapy, the X-ray generation system comprising a linear accelerator system configured to generate an electron beam having an electron beam energy in a range of 6 MeV to 25 MeV and a peak electron beam current during a treatment delivery window in a range of 0.2 A to 10 A, the electron beam configured to impinge a target configured to respond to the incident electron beam by emitting an X-ray beam configured to deliver an X-ray dose rate to the patient in a range of 40 Gy/s to 1000 Gy/s within the treatment delivery window.

2. The X-ray generation system of claim 1, wherein the X-ray dose rate within the treatment delivery window is substantially equal to 400 Gy/s.

3. The X-ray generation system of claim 1, wherein the electron beam has an electron beam energy substantially equal to 10 MeV.

4. The X-ray generation system of claim 1, wherein the electron beam during the treatment delivery window has a pulse length in a range of 4 μs to 400 μs and a duty cycle in a range of 0.001-0.04.

5. The X-ray generation system of claim 4, wherein the electron beam during the treatment delivery window has a pulse length substantially equal to 167 μs, a peak electron beam current on the target substantially equal to 2.1 A, and a duty cycle substantially equal to 0.025.

6. The X-ray generation system of claim 4, wherein the X-ray beam during the treatment delivery window has a repetition rate in a range of 50 Hz to 2500 Hz, a dose rate factor in a range of $1.5 \times 10^4$ cGy/min/mA to $3.0 \times 10^5$ cGy/min/mA, a dose per pulse in a range of 0.02 Gy to 10.0 Gy, and an instantaneous dose rate in a range of $5.0 \times 10^3$ Gy/s to $1.0 \times 10^6$ Gy/s.

7. The X-ray generation system of claim 1, wherein the linear accelerator system comprises an S-band linear accelerator.

8. The X-ray generation system of claim 1, wherein the linear accelerator system comprises an L-band linear accelerator.

9. The X-ray generation system of claim 1, wherein the linear accelerator system comprises an electron source configured to generate electrons and at least one electron accelerating structure configured to receive the electrons from the electron source and to accelerate, bunch, and/or focus the electrons to form the electron beam.

10. The X-ray generation system of claim 9, wherein the linear accelerator system further comprises one or more of the following: one or more pre-accelerator sections; one or more ballistic buncher sections; one or more waveguide buncher sections; one or more chopper sections; one or more solenoids; one or more phase compressor sections; one or more travelling wave or standing wave linear accelerating sections; one or more RF power sources connected to the at least one electron accelerating structure.

11. The X-ray generation system of claim 1, further comprising a gantry and/or an electron optics sub-system configured to move the electron beam such that the X-ray beam impinges the patient along a plurality of directions.

12. The X-ray generation system of claim 11, further comprising a translational and/or rotational stage configured to move the target to increase an area of the target over which a thermal load is imparted by the electron beam to the target.

13. The X-ray generation system of claim 1, wherein the linear accelerator system comprises one or more ballistic buncher sections.

14. An X-ray generation system configured to generate an X-ray beam configured to be delivered to a patient undergoing radiation therapy, the X-ray generation system comprising:
    a controllably rotatable gantry having a rotation axis about which a rotatable portion of the gantry is configured to rotate, the rotation axis configured to extend through the patient undergoing radiation therapy;
    a linac configured to generate an electron beam having an electron beam energy in a range of 6 MeV to 25 MeV and a peak electron beam current during a treatment delivery window in a range of 0.2 A to 10 A;
    a target mounted in or on the rotatable portion of the gantry and configured to generate an X-ray beam in response to being irradiated by the electron beam, the X-ray beam configured to irradiate the patient with an X-ray dose rate in a range of 40 Gy/s to 1000 Gy/s within the treatment delivery window; and
    an electron optics sub-system comprising at least one magnet mounted in or on the rotatable portion of the gantry, the electron optics sub-system configured to direct the electron beam from propagating in a first direction from the linac to propagating in a second direction towards the target.

15. The X-ray generation system of claim 14, wherein the second direction is substantially perpendicular to the first direction within ±10 degrees.

16. The X-ray generation system of claim 14, wherein the linac is mounted in or on the rotatable portion of the gantry.

17. The X-ray generation system of claim 14, wherein the linac is mounted outside or off the rotatable portion of the gantry.

18. The X-ray generation system of claim 17, wherein the at least one magnet comprises a first magnet configured to deflect the electron beam from the linac, a second magnet configured to deflect the electron beam from the first magnet, and a third magnet configured to deflect the electron beam from the second magnet to propagate in the second direction towards the target.

19. The X-ray generation system of claim 14, wherein, with the rotatable portion of the gantry at multiple positions about the rotation axis, the X-ray beam from the target impinges the same target tissue of the patient from different angles.

20. The X-ray generation system of claim 14, wherein the rotatable portion of the gantry is configured to rotate around the patient with a rotation rate greater than 60 rpm.

21. The X-ray generation system of claim 14, wherein the linac comprises one or more ballistic buncher sections.

22. An X-ray generation system configured to generate an X-ray beam configured to be delivered to a patient undergoing radiation therapy, the X-ray generation system comprising:
    a gantry configured to extend at least partially around the patient undergoing radiation therapy;
    a linac configured to generate an electron beam;
    a plurality of targets mounted in or on the gantry, each target of the plurality of targets configured to generate an X-ray beam in response to being irradiated by the electron beam, the X-ray beams from the plurality of targets configured to irradiate the patient; and an electron optics sub-system mounted in or on the gantry, the electron optics sub-system comprising:
- at least one controllably switchable magnet configured to receive the electron beam propagating in a first direction from the linac and to deflect the electron beam into a selected one of two or more second directions; and
- two or more pluralities of magnets, each plurality of magnets of the two or more pluralities of magnets configured to receive the electron beam propagating in one of the two or more second directions from the at least one controllably switchable magnet and to direct the electron beam to propagate in a corresponding third direction towards a target of the plurality of targets.

23. The X-ray generation system of claim 22, wherein the linac is mounted outside or off the gantry.

24. The X-ray generation system of claim 22, wherein the X-ray beams from the plurality of targets impinge the same target tissue of the patient from different angles.

* * * * *